United States Patent
Holger

(10) Patent No.: US 6,767,863 B2
(45) Date of Patent: Jul. 27, 2004

(54) HIGH-STRENGTH LOW-VISCOSITY AGRICULTURAL FORMULATIONS

(75) Inventor: Tank Holger, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 10/324,275

(22) Filed: Dec. 19, 2002

(65) Prior Publication Data

US 2003/0125209 A1 Jul. 3, 2003

Related U.S. Application Data

(60) Provisional application No. 60/324,675, filed on Dec. 21, 2001.

(51) Int. Cl.$^7$ .......................... A01N 25/30; A01N 57/04
(52) U.S. Cl. ...................................... 504/206; 504/365
(58) Field of Search ................................. 504/206, 365

(56) References Cited

U.S. PATENT DOCUMENTS

| | | | |
|---|---|---|---|
| 3,799,758 A | 3/1974 | Franz | 71/86 |
| 4,313,847 A | 2/1982 | Chasin et al. | 252/356 |
| 4,405,531 A | 9/1983 | Franz | 260/501.12 |
| 5,317,003 A | 5/1994 | Kassebaum et al. | 504/116 |
| 5,668,085 A | 9/1997 | Forbes et al. | 504/206 |
| 5,683,958 A | 11/1997 | Berger et al. | 504/116 |
| 5,789,345 A | 8/1998 | Yasui et al. | 504/206 |
| 5,985,798 A | 11/1999 | Crudden | 504/206 |
| 5,998,332 A | 12/1999 | Sato et al. | 504/127 |
| 6,245,713 B1 * | 6/2001 | Brinker et al. | 504/206 |
| 6,277,788 B1 | 8/2001 | Wright | 504/206 |
| 6,365,551 B1 | 4/2002 | Wright et al. | 504/206 |
| 2002/0065199 A1 | 5/2002 | Wright | 504/206 |

FOREIGN PATENT DOCUMENTS

| | | |
|---|---|---|
| EP | 0274369 | 9/1990 |
| EP | 0290416 | 6/1993 |
| WO | WO 97/16969 A1 | 5/1997 |

* cited by examiner

*Primary Examiner*—S. Mark Clardy
(74) *Attorney, Agent, or Firm*—Craig E. Mixan; Woodard, Emhardt, Naughton, Moriarty & McNett

(57) ABSTRACT

The present invention provides a concentrated herbicide composition containing a glyphosate isopropylammonium salt and a polyoxyalkylene alkylamine surfactant. The concentrated herbicide composition can be formulated to exhibit decreased viscosity by reducing the amount of isopropyl amine used to prepare the glyphosate salt while maintaining the high concentration of the glyphosate salt.

8 Claims, No Drawings

HIGH-STRENGTH LOW-VISCOSITY AGRICULTURAL FORMULATIONS

CROSS-REFERENCE TO RELATED APPLICATION

The present application claims the benefit of U.S. Provisional Application Serial No. 60/324,675 filed on Dec. 21, 2001, which is hereby incorporated by reference in its entirety.

BACKGROUND OF THE INVENTION

In general, the present invention relates to agricultural compositions containing glyphosate salts. More specifically, the present invention is directed to agricultural compositions formulated as liquid concentrates containing a glyphosate isopropylammonium salt.

Typically, commercially available agricultural compositions of glyphosate salts are formulated as liquid concentrates that can be readily shipped to consumers. It is desirable to provide a high-strength formulation to reduce shipping and handling costs and to reduce the amount of packaging material that must be disposed. There is often a trade off between providing a highly concentrated herbicide composition to reduce shipping and handling costs and ensuring that the consumer can conveniently use and dilute the concentrate. Increasing the concentration of the active ingredients in the composition can increase the composition's viscosity.

The herbicidal formulations typically include an efficacy-enhancing surfactant. Inclusion of a surfactant is highly desirable because the resulting formulation exhibits a substantially increased herbicidal activity. However, selected surfactants either can interact with the glyphosate salt, increasing the viscosity of the herbicidal formulation, or are generally incompatible with the glyphosate salt solution. Certain surfactants, for example, some of the surfactants in the polyoxyalkylene alkylamine class of compounds, when combined with the glyphosate salt, increase the viscosity of the formulation.

A highly viscous concentrate is difficult for the consumer to use. If the viscosity is too high, handling of the concentrated herbicide can be difficult. Furthermore, highly viscous liquids are difficult to accurately measure, either for application to the plants or for dilution to a less concentrated spray solution. These problems can be further acerbated for agricultural formulations used in the late winter and early spring when the temperatures are generally low. The viscosity of the concentrated agricultural formulations becomes even greater at low temperatures. This makes it even more difficult to dispense or pump and to accurately measure the concentrate.

Additionally, the high-strength formulations should be stable and retain potency during storage and shipping. One or more of the components in a highly concentrated formulation can precipitate or separate from the bulk solution. Consequently, the consumer must redissolve or re-suspend all of the components before use or dilution. It is desirable that the herbicide concentrate be stable at temperatures at least as high as 50° C. and should not exhibit any precipitation or sedimentation at temperatures as low as 0° C.

SUMMARY OF THE INVENTION

Surprisingly it has been found that the viscosity of a concentrated aqueous glyphosate isopropylammonium salt formulation depends upon the molar ratio of glyphosate acid equivalent to isopropylamine. Typically glyphosate isopropylammonium salt concentrates are prepared with about 15%–20% excess isopropylamine, i.e., from a 1.00:1.15 to a 1:00:1.20 molar ratio of glyphosate acid equivalent to isopropylamine. The excess isopropylamine is used to increase the solubility of glyphosate isopropylamine salt at very low temperatures. Generally the glyphosate isopropylammonium salt is prepared as a liquid manufacturing-use concentrate containing 62% glyphosate isopropylammonium salt, which is subsequently formulated into the final product by diluting with water and adding the desired additives, e.g,. an activity enhancing surfactant. A drawback of using the 62% glyphosate isopropylammonium salt manufacturing-use concentrate with an excess of isopropylamine to prepare highly concentrated formulations containing glyphosate isopropylammonium salt in combination with an activity enhancing surfactant is the high viscosity of the resulting product. It has now been found that the viscosity of concentrated glyphosate isopropylammonium formulations can be lowered significantly by using a glyphosate acid equivalent to isopropylamine molar ratio of about 1.00:1.10, and more preferably between about 1:00:1.05, whilst still providing satisfactory stability of the formulation at low temperatures.

The present invention provides a herbicide concentrate comprising: glyphosate isopropylammonium salt, which is dissolved in an aqueous solution at a concentration of greater than about 400 gram acid equivalents per liter (gae/l) based upon glyphosate acid. The glyphosate isopropylammonium salt is prepared by combining glyphosate acid and isopropyl amine at a molar ratio of between about 1.00:1.00 and about 1.00:1.10 (glyphosate acid:isopropyl amine), preferably between 1.00:1.00 and about 1.00:1.05. The concentrate also includes a polyoxyalkylene alkylamine surfactant.

In another form, the present invention provides a herbicide concentrate that comprises an aqueous solution that includes a herbicide component comprising greater than about 400 gae/l of a glyphosate isopropylammonium salt; and a surfactant component including a polyoxyalkylene alkylamine. In this form of the invention the aqueous solution contains less than about 10 molar % excess isopropyl amine, based upon the glyphosate isopropylammonium salt, more preferably the aqueous solution contains less than about 5 molar % excess isopropyl amine, still more preferably the aqueous solution is essentially free of any excess isopropyl amine.

In still yet another form, the present invention provides a method of reducing the viscosity of a concentrated herbicide composition containing a glyphosate salt and a polyoxyalkylene alkylamine surfactant. The method comprises combining glyphosate acid with between about 1 and about 1.10 equivalents of isopropyl amine, based upon the molar equivalents of the glyphosate acid, to provide a glyphosate isopropylammonium salt. The glyphosate isopropylammonium salt is combined with a polyoxyalkylene alkylamine surfactant.

The agricultural formulation provided in the present invention can be formulated and distributed as a highly concentrated solution that exhibits a low viscosity. This formulation can be subsequently diluted to a desired concentration by an end user for use on and around plants.

DESCRIPTION OF THE PREFERRED EMBODIMENTS

The present invention provides highly concentrated agricultural formulations that contain a glyphosate salt and a surfactant. The glyphosate salt is a glyphosate isopropylammonium salt that is specifically formulated to provide a concentrated solution that exhibits low viscosity. The agricultural composition also includes at least one surfactant, preferably a polyoxyalkylene alkylamine surfactant.

It has been determined that a concentrated solution can be prepared by selectively combining about one molar equivalent isopropylamine with about one molar equivalent glyphosate acid in a desired amount of water. The resulting concentrate glyphosate salt composition can be combined with an effective amount of an efficacy-enhancing surfactant. The resulting concentrated solution unexpectedly exhibits a viscosity that is lower than the viscosity of similar compositions, which contain an excess of isopropylamine.

The concentrate of the present invention contains a high concentration of glyphosate as an isopropylammonium salt dissolved in water. In preferred embodiments, the concentration of the glyphosate isopropylammonium salt is selected to be greater than about 400 gram acid equivalents of the glyphosate acid per liter of solution (gae/l), more preferably greater than about 450 gae/l. The upper limit of the glyphosate salt concentration is less than that which would separate out or precipitate from solution at ambient temperature.

The glyphosate salt formulation can be prepared by suspending glyphosate acid in a minimal amount of water and slowly adding one equivalent of isopropylamine to prepare the desired salt solution. Then the surfactant can be added to the clear, homogeneous salt solution. Preferably, the formulation is prepared and maintained below about 50° C. The concentrated formulations of the present invention can also be prepared substantially as described in EP 290, 416 and U.S. Pat. No. 4,612,034—albeit using about a 1:1 molar ratio of glyphosate:isopropylamine instead of using an excess of the amine as prescribed by these references. The resulting formulations were found to be storage stable at a high concentration and higher strength—yet having a low viscosity.

The herbicide concentrate of the present invention can include a slight excess of isopropyl amine. An excess of isopropyl amine is that amount of isopropyl amine greater than the amount of glyphosate initially added to the solution or greater than one equivalent of the glyphosate acid used to prepare the herbicide concentrate. In preferred embodiments, the herbicide concentrate of the present invention includes between about 1.00 equivalents and about 1.10 equivalents isopropyl amine/isopropylammonium cation based on the moles of glyphosate used to initially prepare the herbicide concentrate. More preferably the present invention includes between about 1.00 equivalents and about 1.05 equivalents isopropyl amine/isopropylammonium cation.

The herbicidal concentrate also includes a polyoxyalkylene alkylamine surfactant. Nonlimiting examples of surfactants useful in the present invention include: polyoxyalkylene derivatives of soyamine, tallowamine, and cocoamine. In preferred embodiments of the present invention the surfactant is selected to be a polyoxyalkylene tallow amine or polyoxyalkylene cocoa amine having between 2 and 15 ethylene oxide groups (EO) per amine. More preferred surfactants include a polyoxyalkylene tallow amine or polyoxyalkylene cocoa amine having between 5 and 10 EO per amine.

The herbicidal concentrate also includes a polyoxyalkylene alkylamine surfactant in a herbicidally efficacious amount. More preferably the concentrate includes the surfactant in an amount greater than about 60 grams per liter (g/l), more preferably greater than about 100 g/l. The upper concentration limit of the surfactant is governed by the amount of glyphosate isopropylammonium salt present in the formulation.

The agricultural compositions prepared according to the present invention are highly effective as a herbicide composition against a variety of weeds. The formulations of the present invention can be used as is or combined with other components including other agriculturally acceptable adjuvants commonly used in formulated agricultural products, such as antifoam agents, compatibilizing agents, sequestering agents, neutralizing agents and buffers, corrosion inhibitors, dyes, odorants, penetration aids, wetting agents, spreading agents, dispersing agents, thickening agents, freeze point depressants, antimicrobial agents, crop oil, other biologically and/or agriculturally active components and the like. The concentrated agricultural formulations are typically diluted in water and then applied by conventional means well known to those in the art.

It has been unexpectedly determined that the viscosity of a concentrated glyphosate isopropylammonium salt solution can be varied by altering the amount of isopropyl amine included in the solution. As noted above, commercial herbicide formulations are prepared by reacting glyphosate acid with an excess amount of a base such as isopropyl amine. The present invention provides a highly concentrated glyphosate isopropylammonium salt solution that exhibits significantly reduced viscosity compared with known commercial products having comparable concentrations. In preferred embodiments, the herbicide concentrates of the present invention exhibit a viscosity of less than about 200 cP measured on a Brookfield LVT viscometer with a #2 spindle at 20° C. More preferably the present invention provides a herbicide concentrate having a viscosity of less than about 180 cP, still more preferably less than about 160 cP, measured as above noted.

For the purpose of promoting further understanding and appreciation of the present invention and its advantages, the following examples are provided. It will be understood, however, that these examples are illustrative and not limiting in any fashion.

EXAMPLE 1

Preparation of a Concentrated Glyphosate Formulation

Glyphosate acid (275.2 g technical grade, about 87.2% purity, commonly referred to as a "wet cake") was suspended in 183.9 g of water. Isopropylamine (83.9 g, one (1) equivalent based on the gae of the glyphosate) was slowly added to this glyphosate suspension, while maintaining mixture below about 50° C. to provide a concentrated glyphosate isopropylammonium salt solution. Then 60 g of tallowamine ethoxylate (10 EO) was added to the glyphosate isopropylammonium salt solution. The resulting concentrate had a density of 1.207 g/ml, a pH of 4.58 and contained 480 gae/l glyphosate. The resulting concentrate was found to be a clear, homogeneous solution with a cloud point greater than about 55° C. The resulting concentrate was also stable when stored at −10° C. for 14 days, with no signs of crystallization.

This procedure was followed to prepare additional glyphosate isopropylammonium salt solutions with a glyphosate to isopropylamine (IPA) ratio of approximately 1:1, including those listed in Table 1.

The formulations containing a glyphosate to IPA ratio of approximately 1.00:1.15 were prepared by diluting a commercially available 62% concentrate solution of glyphosate isopropylammonium salt with the required amount of surfactant and water.

EXAMPLE 2
Viscosity Determinations of Glyphosate Formulations

Several glyphosate formulations each with a different surfactant were prepared as described above in Example 1. The viscosity of various glyphosate formulations were determined using a Brookfield LVT viscometer with a #2 spindle at 20° C. The results are summarized in Table 1 below. A commercial formulation, Roundup Spectra Herbicide by Monsanto, which contains 480 gae/l glyphosate as the isopropylamine salt, was used for comparison.

The viscosities for the resulting glyphosate IPA salt formulations are listed in Table 1 below.

TABLE 1

| Herbicide Formulation | Viscosity 1:1.15 Ratio[1] | Viscosity 1:1 Ratio[1] |
|---|---|---|
| Formulation 1 (480 gae/l glyphosate IPA, 120 g/l cocoamine 2EO[2]) | 293 centipoise | 185 centipoise |
| Formulation 2 (480 gae/l glyphosate IPA, 120 g/l cocoamine 15EO[2]) | 290 centipoise | 165 centipoise |
| Formulation 3 (480 gae/l glyphosate IPA, 120 g/l tallowamine 10EO[2]) | 276 centipoise | 122 centipoise |
| Formulation 4 (480 gae/l glyphosate IPA, 150 g/l tallowamine 10EO[2]) | 418 centipoise | 193 centipoise |
| Formulation 5 (480 gae/l glyphosate IPA, 120 g/l tallowamine 20EO[2]) | 187 centipoise | 143 centipoise |
| Roundup Spectra Herbicide (480 gae/l glyphosate IPA) | 259 centipoise | |

[1]glyphosate acid:isopropylamine molar ratio
[2]Units of ethylene oxide groups

As can be seen in the Table 1 above, clearly the 1:1 molar ratio of glyphosate IPA salt formulations have a significantly lower viscosity than the equivalent formulations having the typical 1:1.15 molar ratio of glyphosate acid equivalent to isopropylamine. Furthermore, all formulations at the 1:1 glyphosate acid:isopropylamine ratio have significantly lower viscosity than a commercially sold glyphosate formulation containing an equivalent amount of active ingredient.

EXAMPLE 3
Efficacy of a 1:1 Glyphosate Isopropylammonium Salt Herbicide Formulation The efficacy of a herbicide formulation containing 480 gae/l glyphosate isopropylammonium salt (glyphosate:IPA 1:1 ratio) and 120 g/l tallowamine (10 EO) was compared against a commercially available herbicide sold under the trade name Roundup Ultra Herbicide by Monsanto (356 gae/l glyphosate isopropylammonium salt, plus a full surfactant load) in a greenhouse study over the range of 5 dicot and 3 monocot weed species.

Table 2 summarizes the test results obtained for the formulations 3 and 5 listed in Table 1, compared to the Roundup Ultra Herbicide against 8 different weed varieties: barnyard grass (ECHCG), quack grass (AGGRE), wild oat (AVEFA), wild poinsettia (EPHHL), velvet leaf (ABUTH), morning glory (IPOHE), lambs quarter (CHEAL), and sicklepod (CASOB). The herbicide formulations were applied to the plants at 600 gae/ha (gram acid equivalent per hectare).

Plants were germinated in synthetic soil mix (Metro-mix, manufactured by the O.M. Scott Co.) containing micro nutrients under greenhouse conditions of natural light supplemented by halide light with an average energy of 165 $\mu$mol/m$^2$s, average daylight temperature of 29.4° C. and a relative humidity of 73.7%. The photo-period was 16 hour day and 8 hour night. All plants were top watered prior to treatment and sub-irrigated after treatment. The various plant species were planted to reach two to three leaf stage at the time of spray application of the glyphosate formulations.

All formulations of glyphosate were brought into solution using city tap water. The appropriate amount of formulation was added to 80 ml of water to equal 600 g glyphosate acid equivalent per hectare when applied.

Applications were made with a track sprayer manufactured by Allen Machine Works utilizing an 8002E nozzle at 262 kPa and a track speed of 3.2 km/h. Application height was 45 cm above the plant canopy. This was the equivalent to an application volume of 187 l/ha. All treatments were replicated three times per species. Plants were transferred to the greenhouse for incubation during the duration of the experiment.

Injury and phytotoxicity ratings were visual and taken on each pot at 14 days after application (DAA) with 0% meaning no injury or phytotoxicity and 100% meaning complete kill.

TABLE 2

| | % Control 14 Days after Application of glyphosate isopropylammonium salt at 600 gae/ha | | |
|---|---|---|---|
| Weed Species | Roundup Ultra Herbicide | Formulation 3 | Formulation 5 |
| IPOHE | 51.7 | 61.7 | 60 |
| CHEAL | 97.7 | 97.7 | 94.7 |
| EPHHL | 85 | 86.7 | 91.7 |
| ABUTH | 90 | 99.3 | 100 |
| CASOB | 75 | 73.3 | 94.7 |
| ECHCG | 99.7 | 100 | 100 |
| AGGRE | 55 | 89.7 | 70 |
| AVEFA | 65 | 75 | 83.3 |

The efficacy of the formulations 3 and 5 was at least equivalent to Roundup Ultra Herbicide, and under the greenhouse conditions even demonstrated a marked improvement over the Roundup Ultra Herbicide.

EXAMPLE 4

A series of concentrated herbicide formulations were prepared as described above in Example 1 by combining glyphosate acid (technical grade, as a wet cake) with varying amounts of isopropyl amine ranging from a molar ratio glyphosate acid to isopropyl amine of 1:1 to 1:15. The resulting aqueous solutions were combined with a tallowamine ethoxylate (10 EO) and diluted with a sufficient amount of water to yield a concentrated glyphosate IPA salt formulation with 480 gae/l glyphosate and 110 g/l tallowamine ethoxylate. Table 3 provides a listing of the series of 62% glyphosate isopropylammonium salt components that were used to prepare the formulations, which ultimately contained 480 gae/l glyphosate isopropylammonium salt and 110 g/l tallowamine ethoxylate surfactant.

TABLE 3

| | Molar Ratio of Glyphosate Acid:Isopropyl amine | | | |
|---|---|---|---|---|
| | 1:1.00 | 1:1.05 | 1:1.10 | 1:1.15 |
| Glyphosate wet cake | 104.99 g (0.543 mol) | 104.99 g (0.543 mol) | 104.99 g (0.543 mol) | 104.99 g (0.543 mol) |
| Isopropyl amine | 32.44 g (0.543 mol) | 34.06 g (0.571 mol) | 35.68 g (0.598 mol) | 37.31 g (0.625 mol.) |
| Water | 62.57 g | 60.95 g | 59.32 g | 57.70 g |

The viscosity of the different glyphosate formulations prepared from the glyphosate isopropylammonium salt components listed in Table 3 were determined using a Brookfield LVT viscometer with a #2 spindle at 20° C. The results are summarized in Table 4. It can readily be observed that the formulations containing glyphosate IPA salt prepared with a reduced amount of isopropyl amine exhibit significantly lower viscosities.

TABLE 4

| Herbicide Formulation | Glyphosate:IPA Ratio[1] | Viscosity |
|---|---|---|
| Formulation A (480 gae/l glyphosate IPA, 110 g/l tallowamine 10EO[2]) | 1.00:1.00 | 139 centipoise |
| Formulation B (480 gae/l glyphosate IPA, 110 g/l tallowamine 10EO[2]) | 1.00:1.05 | 158 centipoise |
| Formulation C (480 gae/l glyphosate IPA, 110 g/l tallowamine 10EO[2]) | 1.00:1.10 | 178 centipoise |
| Formulation D (480 gae/l glyphosate IPA, 110 g/l tallowamine 10EO[2]) | 1.00:1.15 | 213 centipoise |

[1]glyphosate acid:isopropylamine molar ratio
[2]Units of ethylene oxide groups

The present invention contemplates modifications as would occur to those skilled in the art. It is also contemplated that the compositions and formulations embodied in the present invention can be modified or combined with other active herbicides, pesticides ant the like, as would occur to those skilled in the art, without departing from the spirit of the present invention. While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of reducing the viscosity of a concentrated herbicide composition containing a glyphosate isopropylammonium salt and an polyoxyalkylene alkylamine surfactant, said method comprising:

combining glyphosate acid in an aqueous slurry with between about 1 and about 1.10 equivalents of isopropyl amine, based upon the molar equivalents of the glyphosate acid, to provide a glyphosate isopropylammonium salt concentrate in the form of a clear, homogeneous aqueous solution; and admixing the glyphosate isopropylammonium salt aqueous solution with the polyoxyalkylene alkylamine surfactant.

2. A herbicide concentrate prepared by the process of claim 1 comprising:

glyphosate isopropylammonium salt dissolved in an aqueous solution at a concentration of greater than about 450 grams acid equivalent per liter; and a polyoxyalkylene alkylamine at a concentration greater than about 60 grams per liter.

3. The concentrate of claim 2 wherein the glyphosate isopropylammonium salt solution is prepared by combining glyphosate acid and isopropyl amine at a molar ratio of between about 1:1 and about 1:1.05.

4. The concentrate of claim 2 wherein the concentration of the polyoxyalkylene alkylamine is greater than about 100 g/l.

5. The concentrate of claim 2 wherein the polyoxyalkylene alkylamine is a polyoxyalkylene tallowamine.

6. The concentrate of claim 2 wherein the polyoxyalkylene alkylamine is a polyoxyalkylene cocoamine.

7. The concentrate of claim 2 wherein the viscosity is less than about 200 cP measured at 20° C.

8. A method of controlling vegetation, said method comprising: contacting the plants with a herbicidal effective amount of a composition prepared by diluting the concentrate of claim 2 with water.

* * * * *

UNITED STATES PATENT AND TRADEMARK OFFICE
CERTIFICATE OF CORRECTION

PATENT NO. : 6,767,863 B2
DATED : July 27, 2004
INVENTOR(S) : Holger Tank

It is certified that error appears in the above-identified patent and that said Letters Patent is hereby corrected as shown below:

Title page,
Item [60], Related U.S. Application Data, should read -- Provisional Application No. 60/342,675… -- rather than "Provisional Application No. 60/324,675…"

Column 1,
Line 8, should read -- sional Application Serial No. 60/342,675 filed on Dec. 21, -- rather than "sional Application Serial No. 60/324,675 filed on Dec. 21,"

Signed and Sealed this

Fourteenth Day of December, 2004

JON W. DUDAS
*Director of the United States Patent and Trademark Office*